United States Patent
Ennis et al.

(10) Patent No.: US 8,299,306 B2
(45) Date of Patent: *Oct. 30, 2012

(54) ACCELERATED SYNTHESIS OF SUBSTITUTED HYDROXYMETHYL PHENOLS

(76) Inventors: Seth C. Ennis, Limerick (IE); Bryan D. Kennedy, County Roscommon (IE)

( * ) Notice: Subject to any disclaimer, the term of this patent is extended or adjusted under 35 U.S.C. 154(b) by 433 days.

This patent is subject to a terminal disclaimer.

(21) Appl. No.: 12/303,660

(22) PCT Filed: Jun. 4, 2007

(86) PCT No.: PCT/EP2007/004928
§ 371 (c)(1), (2), (4) Date: Dec. 5, 2008

(87) PCT Pub. No.: WO2007/140965
PCT Pub. Date: Dec. 13, 2007

(65) Prior Publication Data
US 2010/0174107 A1   Jul. 8, 2010

(30) Foreign Application Priority Data
Jun. 8, 2006   (EP) ..................... 06011838
Jun. 8, 2006   (IE) .................... S2006/0424

(51) Int. Cl.
*C07C 211/00* (2006.01)
(52) U.S. Cl. ..................................... 564/316
(58) Field of Classification Search ............ None
See application file for complete search history.

(56) References Cited

U.S. PATENT DOCUMENTS

| | | | | |
|---|---|---|---|---|
| 5,750,766 | A * | 5/1998 | Krummel et al. | 560/82 |
| 6,713,464 | B1 * | 3/2004 | Meese et al. | 514/175 |
| 6,858,650 | B1 * | 2/2005 | Meese | 514/530 |

FOREIGN PATENT DOCUMENTS

| | | | |
|---|---|---|---|
| CN | 1654452 A * | 8/2005 | |
| EP | 1582523 | 10/2005 | |
| WO | 94/11337 | 5/1994 | |
| WO | 99/58478 | 11/1999 | |
| WO | 01/35957 | 5/2001 | |

OTHER PUBLICATIONS

Carey, et al. "Advanced Organic Chemistry." 4th Edition, 2000, pp. 447-448.
Smith, et al. "March's Advanced Organic Chemistry." 5th Edition, 2001, p. 1214.

* cited by examiner

*Primary Examiner* — Sudhakar Katakam
(74) *Attorney, Agent, or Firm* — Kenyon & Kenyon LLP

(57) ABSTRACT

This disclosure relates to process for the preparation of a compound of formula (I) wherein R is hydrogen, a straight or branched $C_1$-$C_6$ alkyl-carbonyl group or a phenylcarbonyl group, or a salt thereof, comprising the following steps: a) adding to a suspension of Mg a compound of formula (II) $R^1(MgX)_n$—LiY wherein n is 1 or 2; $R^1$ is an aromatic, aliphatic, carbocyclic or heterocyclic organic group having 1 to 24 carbon atoms; X and Y are independently selected from Cl, Br and I, b) reacting said reaction mixture with a suitable halogenated compound in a solvent to form a Grignard reagent, c) reacting said Grignard reagent with a suitable linear, branched or cyclic carbonate to obtain a compound of formula (IV) wherein A is a linear, branched or cyclic $C_1$-$C_6$ alkyl group, and preferably a methyl group, and then further reacting the compound of formula (IV) in a known manner to obtain a compound of formula (I) and optionally salt formation.

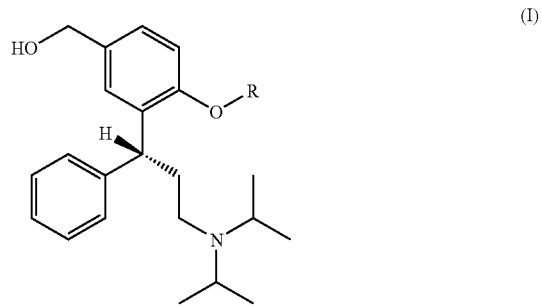

(I)

24 Claims, No Drawings

ACCELERATED SYNTHESIS OF SUBSTITUTED HYDROXYMETHYL PHENOLS

CROSS REFERENCE TO RELATED APPLICATION

This application is a 371 of International Patent Application No. PCT/EP2007/004928, filed Jun. 4, 2007, which claims priority to European Patent Application No. 06011838, filed Jun. 8, 2006, and Irish Patent Application No. S2006/0424, filed Jun. 8, 2006. The contents of these applications are hereby incorporated by reference in their entireties.

FIELD

Presently described is a process for the preparation of 2-(3-diisopropylamino-1-phenylpropyl)-4-(hydroxymethyl) phenol which is known as the active metabolite of tolterodine (hereafter named the "Active Metabolite") and its phenolic monoesters by a improved synthetic route via a so-called "Turbo Grignard" reaction. The target compounds have the following formula (I):

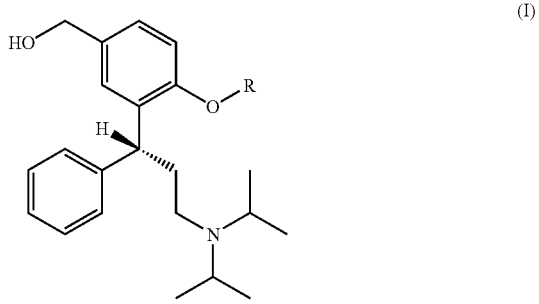

(I)

wherein R is hydrogen, a straight or branched $C_1$-$C_6$ alkyl-carbonyl group or a phenylcarbonyl group. If R in formula (I) is hydrogen, the formula represents the Active Metabolite.

A particular preferred example of a monoester of formula (I), wherein R is an isopropylcarbonyl group, is Fesoterodine which can be chemically defined as R-(+)-Isobutyric acid 2-(3-diisopropylamino-1-phenylpropyl)-4-(hydroxymethyl) phenol ester. It has the formula (Ia) depicted below.

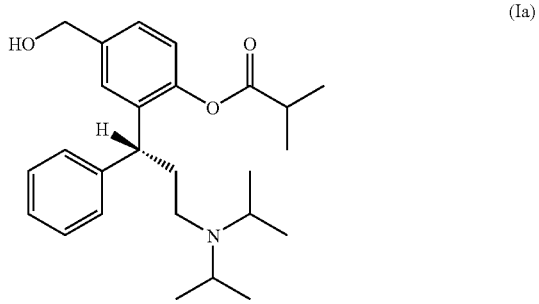

(Ia)

The Active Metabolite and its phenolic monoesters of formula (I) are known from WO 99/058478.

Also described herein is a process for the preparation of salts of the compounds of formula (I), specifically including the preparation of salts of Fesoterodine of formula (I), and more particularly the preparation of the hydrogen fumarate salt of Fesoterodine.

Further disclosed is the preparation of pharmaceutical formulations containing compounds of formula (I), such as Fesoterodine, and the preparation of pharmaceutical formulations containing a pharmaceutically acceptable salt of any of the compounds of formula (I), including, for example, the hydrogen fumarate or hydrochloride hydrate salts of Fesoterodine.

BACKGROUND

In man, normal urinary bladder contractions are mediated, in part, through cholinergic muscarinic receptor stimulation. Muscarinic receptors not only mediate, in part, normal bladder contractions, but also may mediate the main part of the contractions in the overactive bladder resulting in symptoms such as urinary frequency, urgency and urge urinary incontinence.

After administration of Fesoterodine and other phenolic monoesters of formula (I) to mammals, such as humans, these compounds are cleaved to form the Active Metabolite within the body. The Active Metabolite is known to be a potent and competitive muscarinic receptor antagonist (WO 94/11337). Fesoterodine and other phenolic esters of the formula (I) thus represent potential prodrugs for the Active Metabolite, and are effective drugs for the treatment of overactive bladder with symptoms of urge urinary incontinence, urgency, and urinary frequency, as well as detrusor hyperactivity (as described in U.S. Pat. No. 6,713,464 and EP-B-1,077,912).

A synthetic approach for the production of the Active Metabolite and monoesters of the phenolic hydroxy group of the Active Metabolite such as Fesoterodine has been described in U.S. Pat. No. 6,713,464 as follows:

In a first step, an ethereal solution is prepared from R-(−)-[3-(2-benzyloxy-5-bromophenyl)-3-phenylpropyl]-diisopropylamine, ethyl bromide and magnesium; this solution is diluted with dry THF and is cooled to −60 C.

In a second step, powdered solid carbon dioxide is added in small portions and the reaction mixture is warmed to room temperature.

In a third step, the reaction is quenched with an aqueous solution of ammonium chloride.

In a fourth step, the aqueous phase of the quenched reaction mixture is adjusted to pH 0.95.

In a fifth step, the pH adjusted phase is filtered and R-(−)-4-benzyloxy-3-(3-diisopropylamino-1-phenylpropyl)-benzoic acid hydrochloride can be recovered from the solid.

In a sixth step, the resulting purified benzoic acid is esterified to its corresponding methyl ester. A diagram summarizing this multi-step synthesis is shown below.

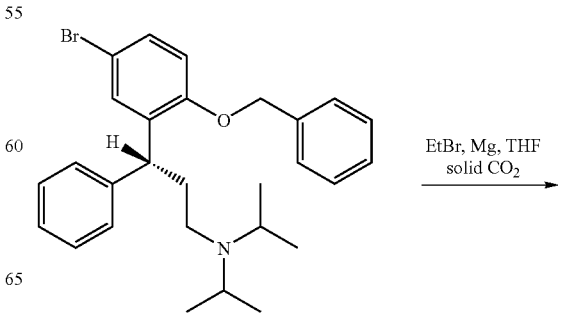

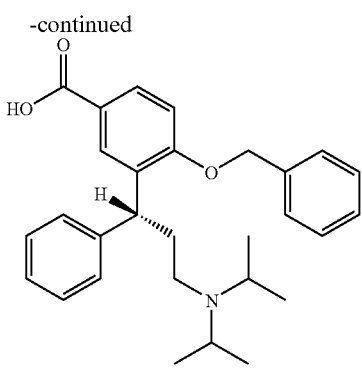

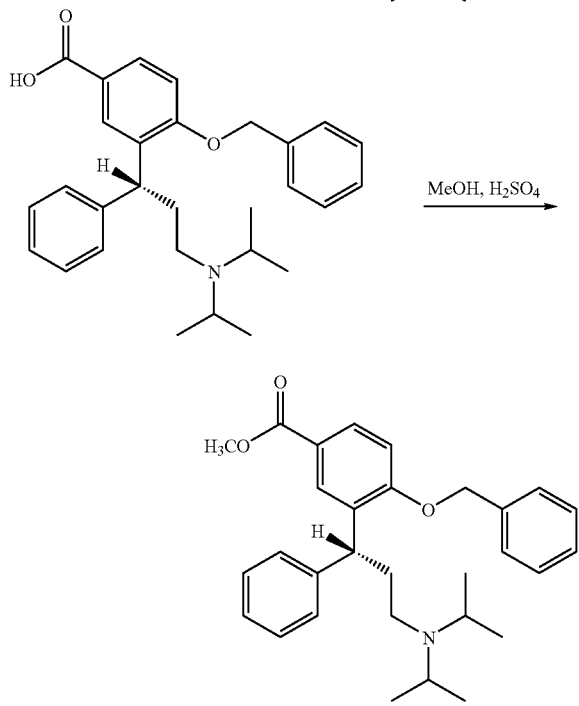

U.S. Pat. No. 6,713,464 further describes converting the methyl ester to the Active Metabolite, and then esterifying the Active Metabolite to a phenolic monoester, such as Fesoterodine.

WO 94/11337 also describes a multi-stage process to synthesize the precursor to the Active Metabolite.

These previously described methods for producing the Active Metabolite require numerous steps that result in complex purification procedures, time-delay, and enhanced possibility of human error, thereby prohibiting optimal efficiency and cost-effectiveness. Also, the solid carbon dioxide used in the art is difficult to handle on large scale due to the need to work at very low temperatures and to add the crushed dry ice portion wise, and due to the difficulties to control the very exothermic nature of the reaction.

The present disclosure aims to overcome these problems and disadvantages. It has been found, and this forms one aspect of the present disclosure, that the use of a di($C_1$-$C_6$ alkyl)carbonate, preferably dimethylcarbonate, in the Grignard reaction results in a highly pure product, while at the same time eliminating the production of the benzoic acid and the purification thereof.

This is surprising since current and well-known textbooks teach that the addition of Grignard reagents to carbonates and other esters produces tertiary alcohols as a predominant product. For example, in F. A. Carey, R. J. Sundberg, "Advanced Organic Chemistry", Springer Media, 2001, it is taught that the addition of Grignard reagents to esters (including carbonates) is commonly used to produce tertiary alcohols (pages 447-448). Likewise, the well-known compendium "March's Advanced Organic Chemistry", Wilex-Interscience Publication, John Wiley & Sons, Inc., $5^{th}$ edition, 2001, page 1214, teaches that in Grignard reactions "carbonates give tertiary alcohol in which all three R groups are the same" (page 1214).

In a second aspect of the presently disclosed method, a further increase in reaction speed, yield and purity was achieved using a combination of a so-called Turbo Grignard reagent and extra Magnesium in such a Grignard reaction.

Recently, Knochel and co-workers (EP 1 582 523) described a reagent for use in the preparation of organomagnesium compounds, which reagent is designated as "Turbo Grignard reagent" in this application. They found that by using a mixed organometallic compound of the following formula (II)

$$R^1(MgX)_n \cdot LiY \quad (II)$$

wherein n is 1 or 2; $R^1$ is a substituted or unsubstituted $C_{4-24}$-aryl or $C_{3-24}$-heteroaryl, containing one or more heteroatoms as B, O, N, S, Se or P; linear or branched, substituted or unsubstituted $C_{1-20}$ alkyl, $C_{1-20}$ alkenyl, $C_{1-20}$ alkynyl; or substituted or unsubstituted $C_{3-20}$ cycloalkyl; or a derivative thereof; X and Y are independently or both Cl, Br or I, preferably Cl;

a fast exchange reaction occurs leading to the desired Grignard reagents in high yields under mild conditions and allowing the preparation of many functionalized Grignard compounds which were previously only available via Br/Mg-exchange reactions in mediocre yields.

Conversions which were conducted with e.g. iPrMgCl·LiCl resulted in improved yields and in a shortened reaction time with high purity. Although the mechanism of the catalysis is not elucidated, Knochel et al. assumed that the role of lithium chloride is to activate iPrMgCl by increasing the nucleophilic character of the isopropyl group by forming a magnesiate species leading via an intermediate finally to the organomagnesium species PhMgCl.LiCl.

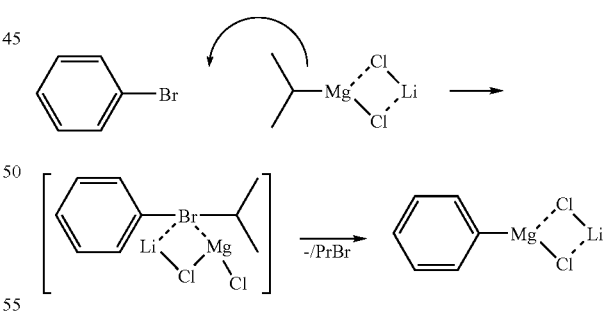

The complexation of the arylmagnesium may be responsible for the enhanced reactivity of these magnesium organometallics.

The present application discloses that the use of iPrMgCl·LiCl in conjunction with additional Mg in the process of preparing of 2-(3-diisopropylamino-1-phenylpropyl)-4-(hydroxymethyl)-phenol ("Active Metabolite") and its phenolic monoesters of formula (I) results in a increased yield and purity in comparison to conventional Grignard reagents or compared to the sole use of Turbo Grignard reagents without extra Mg. When the Turbo Grignard reagent was used solely, long reaction times were required and thus a great risk of impurity formation, in particular due to moisture ingress and subsequent formation of a des-bromo by-product. Surprisingly, the addition of magnesium resulted in a marked increase in both reaction rate and subsequent overall reaction yield and purity and thus provides a more efficient synthetic approach to compounds of formula (I).

SUMMARY

Described herein is an improved process for the preparation of the Active Metabolite and its phenolic monoesters of formula (I) including particularly Fesoterodine and its salts, particularly its hydrogen fumarate salt:

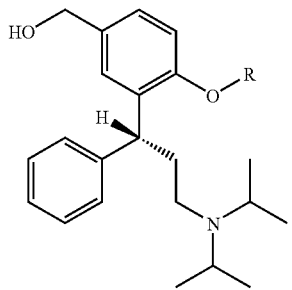
(I)

wherein R is hydrogen, a straight or branched $C_1$-$C_6$ alkylcarbonyl group or a phenylcarbonyl group.

The inventive synthesis is characterized by the steps of:
a) adding to a suspension of Mg a compound of formula (II)

$$R^1(MgX)_n \cdot LiY \quad (II)$$

wherein n is 1 or 2; $R^1$ is an aromatic, aliphatic, carbocyclic or heterocyclic organic group having 1 to 24 carbon atoms; X and Y are independently selected from Cl, Br and I, b) reacting said reaction mixture with a compound of formula (III)

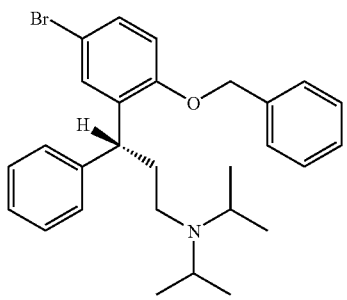
(III)

in a solvent to form a Grignard reagent,
c) reacting said Grignard reagent with a suitable linear, branched or cyclic carbonate, preferably with a di($C_{1-6}$ alkyl)carbonate, and most preferably with dimethylcarbonate to obtain a compound of formula (IV)

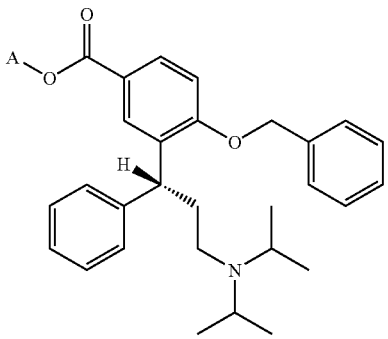
(IV)

wherein A is a linear, branched or cyclic $C_1$-$C_6$ alkyl group, and preferably a methyl group,
and then further reacting the compound of formula (IV) in a known manner to obtain a compound of formula (I) and optionally salt formation.

According to one aspect of the present disclosure, it was surprisingly found that the addition of Mg to the Turbo Grignard reagent of formula (II) results in a better yield, shortened reaction time and higher purity as compared with the use of the Turbo Grignard reagent alone.

DETAILED DESCRIPTION

The improved synthesis of the compounds of formula (I) via a Turbo Grignard reagent in the presence of additional Mg, is now described in greater detail with reference to preferred embodiments.

In step a) a compound of formula (II)

$$R^1(MgX)_n \cdot LiY \quad (II)$$

is added to a suspension of Mg in suitable solvent. The suspension may be in the form of Mg turnings or Mg powder in an inert solvent. Preferred solvents for this step are ethers such as diethylether, diisopropylether or cyclic ethers. Most preferred is tetrahydrofurane (THF).

In formula (II), $R^1$ is an aromatic, aliphatic, carbocyclic or heterocyclic organic group having 1 to 24 carbon atoms. Preferably $R^1$ is a substituted or unsubstituted $C_{4-24}$ aryl or $C_{3-24}$ heteroaryl group, containing one or more heteroatoms selected from B, O, N, S, Se or P; a linear or branched, substituted or unsubstituted $C_{1-20}$ alkyl, $C_{1-20}$ alkenyl, $C_{1-20}$ alkynyl; or a substituted or unsubstituted $C_{3-20}$ cycloalkyl group; or a derivative thereof. The substituents in the above mentioned groups can be selected from alkyl, cycloalkyl, alkenyl, alkoxy, aryl groups, but substituents that might interfere with the Grignard reaction (such as OH— or NH— groups or reducible groups) should generally be avoided. In another preferred aspect, $R^1$ is an unsubstituted $C_{1-6}$ alkyl.

Particular compounds of formula (II) are adducts of methylmagnesium chloride and lithium chloride, and adducts of isopropylmagnesium chloride and lithium chloride (iPrMgCl.LiCl), with iPrMgCl.LiCl being most preferred.

Preferably, reaction step a) is carried out in an inert atmosphere, preferably a nitrogen or argon atmosphere. Step a) can be divided up into:
a1) preparing a suspension of Mg in a suitable solvent, and
a2) adding to said suspension a compound of formula (II), preferably in an amount of 1.0 to 5.0 molar equivalents, more preferably 1.0 to 2.0 equivalents, particularly in about 1.5 equivalents, based on the compound of formula (III).

The ratio of Mg and the compound of formula (II) may vary in a range from 1:5 to 50:1, more preferably 1:2 to 10:1, even more preferably 1:1.5 to 2:1, and most preferably the ratio is about 1:1 (in mol equivalents).

A part of the solvent used to suspend the Mg in step a1), may be removed by distillation, such as azeotropic distillation, before the Grignard reagent is added. This distillation can remove up to about 50% to about 60% of the solvent. The solvent distillation also removes water, which can minimize the formation of a des-bromo amine impurity.

In a preferred embodiment step a1) is therefore carried out at elevated temperature to remove part of the solvent by distillation, followed by a decrease of temperature, preferably to below 50° C., more preferably to below 40° C., and most preferably to a temperature between 30° C. and 35° C. The reaction mixture may then be aged for 2-5 hours, preferably 1-2 hours.

In a preferred embodiment of the present disclosure the addition of the compound of formula (II) in step a2) is conducted dropwise. Furthermore it is preferred to increase the reaction temperature to about 45-55° C. after the complete addition of the solution containing a compound of formula (II).

In step b) the reaction mixture is reacted with a compound of formula (III)

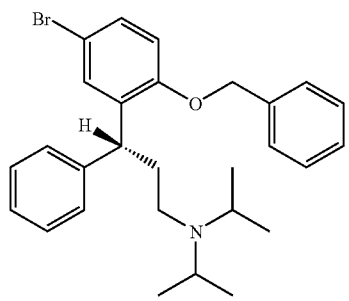

(III)

in a solvent to form a Grignard reagent.

In a preferred embodiment the addition of a solution comprising a compound of formula (III) is conducted dropwise.

The formation of the Grignard reagent as described in step b) is preferably carried out in a temperature range of about 40 to 80° C. and most preferably in a temperature range of about to about 70° C. The reaction can be conducted under agitation (e.g. stirring) up to completion.

A preferred solvent in reaction step b) is toluene, but other suitable organic solvents known to those skilled in the art can be used as well. Preferably the water content in the solution containing compound (III) is not more than about 0.1 wt % and most preferably not more than about 0.05 wt %.

In step c) the Grignard reagent is reacted with a suitable carbonate such as a cyclic $C_1$-$C_6$ alkylene carbonate or a dialkyl carbonate (wherein the alkyl chain can be branched, linear or cyclic), preferably a di($C_1$-$C_6$ alkyl)carbonate, and preferably with dimethylcarbonate to obtain a compound of formula (IV) depicted below wherein A is a linear, branched or cyclic $C_{1-6}$ alkyl chain, and preferably a methyl group.

An excess of carbonate as compared to a compound of formula (III) is preferred, e.g. an about 1.1-fold to about 50-fold molar excess of carbonate, and an about 5-fold to about 50-fold molar excess is particularly preferred.

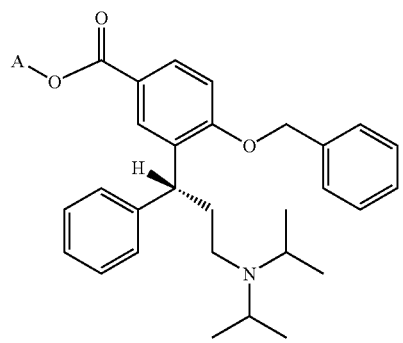

(IV)

Dimethylcarbonate is the most preferred carbonate.

However, other di($C_{1-6}$ alkyl)carbonates, wherein the "alkyl" residues may represent a saturated straight, branched or cyclic hydrocarbon chain, such as for example diethylcarbonate may also be used. Other suitable carbonates include cyclic $C_{1-6}$ alkylene carbonates such as ethylene carbonate or propylene carbonate.

A preferred solvent for step c) is hexane, however, any inert solvent with a boiling point below the boiling point of the carbonate and which is capable of forming an azeotrop with water, including heptane, hexane-isomers and suitable mixtures thereof, can be used.

A part of the hexane used to dissolve dimethylcarbonate, may be removed by distillation, such as azeotropic distillation, before the Grignard reagent is added. This distillation can remove up to about 90% to about 95% of the hexane. The solvent distillation also removes water, which can minimize the formation of a des-bromo amine impurity. Preferably, the water content of the distilled di($C_1$-$C_6$ alkyl)carbonate solvent mixture should be no more than about 0.1 wt %, and more preferably no more than about 0.05 wt %, even more preferably no more than about 0.01 wt %.

In the most preferred embodiment of the present disclosure, the reaction of the Grignard reagent with dimethylcarbonate is carried out at a temperature below about 10° C., under agitated conditions. After complete addition of dimethylcarbonate the resulting solution is preferably heated to ambient temperature upon stirring. The preferred stirring time is about 1 hour.

Step c) is completed by quenching the reaction mixture with a suitable reagent. A preferred quenching reagent is aqueous $NH_4Cl$, although other quenching agents known to those skilled in the art may be used, including aqueous ethyl acetate, aqueous NaCl or aqueous hydrochloride acid solution. After suitable workup procedures comprising for example the steps of removal of insoluble inorganic salts (e.g. by centrifugation or filtration); washing with water to remove dissolved inorganic salts; then azeotropic drying; removal of organic phase by distillation and crystallization in 2-propanol a compound of formula (IV) can be isolated, typically after crystallisation in a suitable solvent such as isopropyl alcohol.

The compound of formula (IV) can then be further reacted, if desired, to obtain a compound of formula (I).

A particularly preferred embodiment of the present disclosure is a process for the preparation of a compound of formula (I) including the Active Metabolite, and, if desired, its phenolic monoesters including particularly Fesoterodine or a salt thereof, preferably a pharmaceutically acceptable salt of Fesoterodine, and most preferably the hydrogen fumarate salt of Fesoterodine, which process includes the steps of:

a1) preparing a solution of 1-2 molar equivalents, preferably 1.5 molar equivalents Mg, (based on the compound of formula (III)) in tetrahydrofuran, and a2) adding to said solution 1-2, preferably 1.5 mol-equivalents of iPrMgCl.LiCl (based on the compound of formula (III)), b) reacting the reaction mixture of step a2) with a compound of formula (III), and optionally raising the temperature of said reaction mixture to a temperature of 40-50° C., and c) reacting the resulting Grignard reagent with an excess of dimethylcarbonate in hexane, at a reaction temperature of below about 10° C. and at an agitation speed of about ≧90 rpm, followed by quenching the thus obtained mixture with an aqueous NH₄Cl solution to obtain a compound of formula (IV). This compound can then be isolated and purified as described above.

After formation of the compound of formula (IV), one option is to further react the compound of formula (IV) to obtain a compound of formula (I). This can be accomplished, for example, as follows:

d) reducing the methylester to the corresponding methylalcohol, and

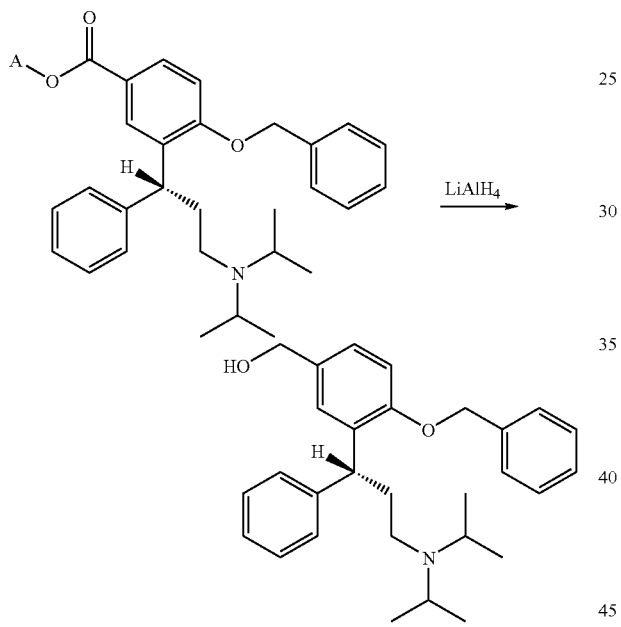

e) debenzylating the protected alcohol to form the Active Metabolite mentioned above.

Another option is to convert the Active Metabolite to an ester thereof such as Fesoterodine or a salt of Fesoterodine, preferably the hydrogen fumarate salt of Fesoterodine, by:

f) phenolic monoacylation, and

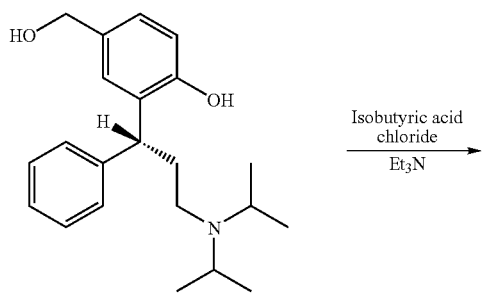

g) salt formation

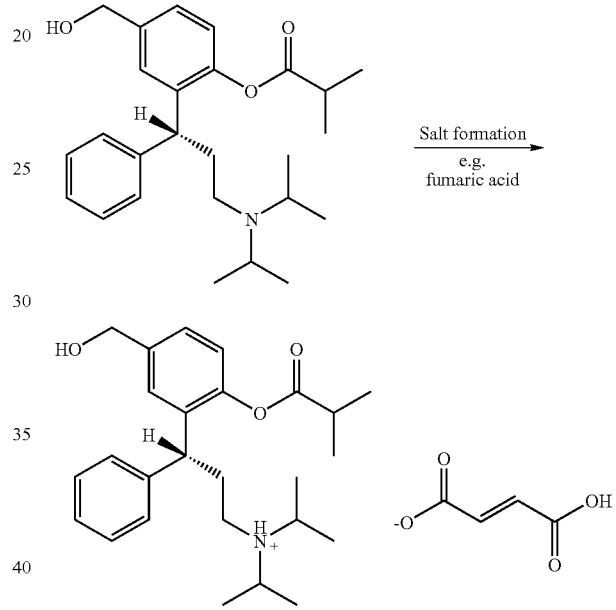

The formation of other phenolic monoesters of the Active Metabolite is possible by using respective other organic acid halides in step f) of the above scheme. Examples of steps d) to g) are disclosed e.g. in U.S. Pat. No. 6,858,650.

The final compound (I) or (Ia) (phenolic monoesters of the Active Metabolite including Fesoterodine or pharmaceutically acceptable salts thereof) can then be formulated in a known manner to obtain an oral, parenteral, or transdermal medicament.

The present disclosure also relates to compounds of formula (I) and (IV) that are obtained by any of the processes disclosed herein. Even further described are pharmaceutical compositions containing compounds of formula (I), and more specifically of formula (Ia) that are obtained by any of the processes disclosed herein.

The present disclosure is further illustrated by the following non-exhaustive examples. The examples do not intend to limit the scope of this disclosure as defined in the claims below. The starting compound of formula (III) can be prepared in a known manner, e.g. such as described in the Experimental Part of U.S. Pat. No. 6,713,464.

EXAMPLES

Example 1

Preparation of R-(−)-4-benzyloxy-3-(3-diisopropylamino-1-phenylpropyl)-benzoic methylester (IV) with a mixture of 1.5 equivalents Mg and 1.5 equivalents of iPrMgCl.LiCl Magnesium turnings (1.15 g, 47.3 mmol) and THF (120 ml) were charged to a 250 ml round bottomed flask with an agitator, dropping funnel, thermometer, nitrogen inlet and distillation apparatus applied. The system was purged with nitrogen and the mixture distilled to a target volume of 55 ml to 60 ml. The contents of the flask were cooled to 30° C. to 35° C. in a nitrogen atmosphere and aged for 1 to 2 hour. iPrMg-Cl.LiCl (37.5 ml, 47.3 mmol) was charged via a syringe to the flask. The temperature was adjusted to 50° C. and the toluene solution of R-(−)-[3-(2-Benzyloxy-5-bromophenyl)-3-phenylpropyl]-diisopropylamine (III) (15 ml, 31.22 mmol) (prepared from R-(−)-3-(2-Benzyloxy-5-bromophenyl)-3-phenylpropionic acid by the procedure described in U.S. Pat. No. 6,713,464) was charged dropwise via a pressure equalising funnel to the reaction mixture. No exotherm was observed. The temperature of the flask was adjusted to reflux (66° C.). The reaction was agitated for 2 hours at which stage analysis indicated reaction completion (NMT 0.5% (III) with respect to des-bromo amine).

Hexane (200 ml) and dimethyl carbonate (80 ml) were charged to a 500 ml round bottomed flask equipped with a distillation apparatus and thermometer. The solution was reduced in volume to 160 ml. The solution was then cooled to 0° C. to 5° C. under nitrogen. The reaction solution was cooled to 0° C. to 5° C. and was charged to the dimethyl carbonate and hexane solution using a syringe, maintaining the temperature less than 10° C. The resulting green suspension was heated to 25° C. to 30° C. and agitated for 1 hour. The mixture was sampled for reaction completion. The reaction mixture was cooled to 10° C. to 15° C. and 10% ammonium chloride (38 ml) was charged maintaining the temperature between 10° C. to 15° C. while agitating. The resulting mixture was agitated for a minimum of 30 minutes.

The biphasic mixture was transferred to a separating funnel and the lower aqueous layer was disposed of after confirming its pH was above 7. The organic layer was washed twice with water (2×38 ml). The organic layer was transferred to a 2 L flask equipped with an agitator, thermometer, Dean-Stark apparatus, and condenser and maintained under a nitrogen atmosphere throughout. The solution was heated to reflux and azeotropically dried until no further water was collected. The volume of the solution was reduced to 50 to 54 ml by atmospheric distillation. Isopropanol was charged to the flask and distillation was repeated to a volume of 50 ml to 54 ml. Another isopropanol charge was made and the solution again distilled to 50 ml to 54 ml. The agitated solution was slowly cooled to 20° C. to 25° C. and aged for 2 hours by which stage precipitation of product was observed. The suspension was agitated for a further 2 hours after precipitation. The suspension was cooled to 0° C. to 5° C. and aged for 2 hours.

The product was isolated by filtration on a Buchner funnel and the flask and product were washed twice with cold isopropanol (0° C., 6 ml). R-(−)-4-benzyloxy-3-(3-diisopropylamino-1-phenylpropyl)-benzoic methylester (IV) was dried in a vacuum oven at 40° C. until constant weight was obtained (12 hours). The product was obtained in 61% yield with a purity of 99.13%.

Example 2

Preparation of R-(−)-4-benzyloxy-3-(3-diisopropylamino-1-phenylpropyl)-benzoic methylester (IV) with 3.0 equivalents of iPrMgCl.LiCl An experiment was carried out according to the procedure of Example 1, but using 3.0 equivalents of the Turbo Grignard reagent but no extra Mg. No further improvement in yield or quality was observed compared with Example 1.

The invention claimed is:

1. A process for the preparation of a compound of formula (I)

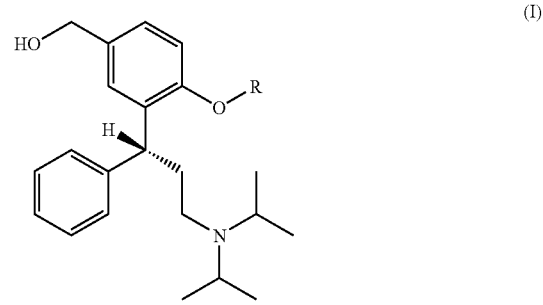

(I)

wherein R is hydrogen, a straight or branched $C_1$-$C_6$ alkylcarbonyl group or a phenylcarbonyl group, or a salt thereof, comprising the following steps:

a) forming a reaction mixture by adding to a suspension of Mg a compound of formula (II)

$R^1(MgX)_n \cdot LiY$ (II)

wherein n is 1 or 2; $R^1$ is an aromatic, aliphatic, carbocyclic or heterocyclic organic group having 1 to 24 carbon atoms; X and Y are independently selected from Cl, Br and I, b) reacting the reaction mixture with a compound of formula (III)

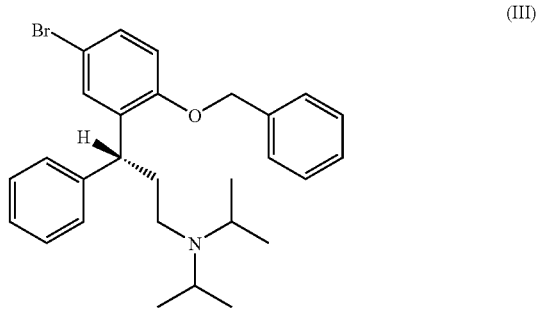

(III)

in a solvent to form a Grignard reagent, c) reacting the Grignard reagent with a linear, branched or cyclic carbonate to obtain a compound of formula (IV)

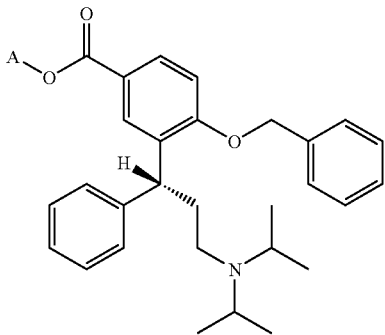

wherein A is a linear, branched or cyclic $C_1$-$C_6$ alkyl group, and then further reacting the compound of formula (IV) to obtain a compound of formula (I) by reducing the ester to the corresponding methyl alcohol and (i) debenzylating the protected alcohol when R is hydrogen or (ii) debenzylating the protected alcohol and then carrying out phenolic monoacylation when R is $C_1$-$C_6$ alkylcarbonyl or phenylcarbonyl.

2. The process of claim 1, wherein the compound of formula (I) is converted into a salt.

3. The process of claim 1, wherein A is a methyl group.

4. The process of claim 1, wherein the compound of formula (I) is Fesoterodine having the formula (Ia)

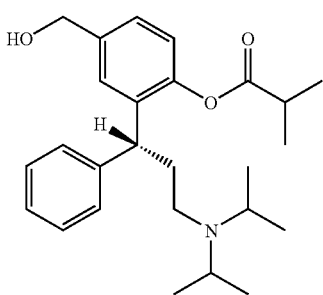

or a salt thereof.

5. The process of claim 4, wherein the compound of formula (I) is the hydrogen fumarate salt of Fesoterodine.

6. The process of claim 1, wherein a cyclic $C_1$-$C_6$ alkylene carbonate or a $C_1$-$C_6$ dialkyl carbonate is used in step c).

7. The process of claim 1, wherein dimethylcarbonate is used in step c) in about 1.1-fold to 50-fold molar excess compared to the amount of compound of Formula (III).

8. The process of claim 1, wherein a solvent is used in step c).

9. The process of claim 8, wherein the solvent is hexane.

10. The process of claim 9, wherein in step c) dimethylcarbonate is dissolved in hexane and then distilled to reduce the water content to 0.01% or below and then the Grignard reagent is added.

11. The process of claim 1, wherein the reaction step c) is followed by quenching the mixture with a reagent.

12. The process of claim 11, wherein the reagent is aqueous $NH_4Cl$.

13. The process of claim 1, wherein step a) is conducted by a1) preparing a suspension of Mg in a solvent, and a2) adding to the suspension a compound of formula (II).

14. The process of claim 13, wherein the solvent in step a1) is THF.

15. The process of claim 13, wherein compound (II) is added in an amount of 1.0 to 5.0 equivalents, based on the compound of formula (III).

16. The process of claim 13, wherein compound (II) is added in an amount of 1.0 to 2.0 equivalents, based on the compound of formula (III).

17. The process of claim 13, wherein compound (II) is added in an amount of 1.5 equivalents, based on the compound of formula (III).

18. The process of claim 1, wherein the compound of formula (II) is iPrMgCl.LiCl.

19. A process for the preparation of a pharmaceutical composition containing FesOterodine hydrogen fumarate comprising the steps of
(i) preparing Fesoterodine hydrogen fumarate by the process of claim 5, and
(ii) formulating the thus obtained Fesoterodine hydrogen fumarate to obtain a pharmaceutical composition.

20. The process of claim 1 wherein:
(i) the suspension of Mg is in an inert solvent,
(ii) the solvent of step b) is toluene, and
(iii) step c) is carried out in a solvent selected from the group consisting of hexane, heptane, hexane-isomers, and mixtures thereof.

21. The process of claim 20 wherein the inert solvent is an ether.

22. The process of claim 21 wherein the ether is selected from the group consisting of diethyl ether, diisopropyl ether, and cyclic ethers.

23. The process of claim 1 wherein the Mg in the suspension of Mg in step a) is present at 1-2 molar equivalents based on the compound of formula (III).

24. The process of claim 23 wherein the Mg in the suspension of Mg in step a) is present at 1.5 molar equivalents based on the compound of formula (III).

* * * * *